(12) United States Patent
Eliasson

(10) Patent No.: US 8,194,819 B2
(45) Date of Patent: Jun. 5, 2012

(54) MAMMOGRAPHY METHOD AND MAMMOGRAPHY APPARATUS

(75) Inventor: Eva Eliasson, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 213 days.

(21) Appl. No.: 12/778,606

(22) Filed: May 12, 2010

(65) Prior Publication Data

US 2010/0290585 A1    Nov. 18, 2010

(30) Foreign Application Priority Data

May 13, 2009 (DE) .................. 10 2009 021 023

(51) Int. Cl.
*A61B 6/04* (2006.01)
*H01J 31/50* (2006.01)

(52) U.S. Cl. ........................... 378/37; 378/189

(58) Field of Classification Search ............... 378/4–26, 378/37, 189, 210
See application file for complete search history.

(56) References Cited

U.S. PATENT DOCUMENTS

| 3,609,355 A | 9/1971 | Schwarzer |
| 2006/0262898 A1* | 11/2006 | Partain et al. ................. 378/37 |
| 2008/0077005 A1* | 3/2008 | Piron et al. .................. 600/411 |

* cited by examiner

*Primary Examiner* — Anastasia Midkiff
(74) *Attorney, Agent, or Firm* — Schiff Hardin LLP

(57) ABSTRACT

In a mammography method and a mammography apparatus to generate x-ray images of a breast, a support unit is positioned between the breasts. In the support unit two x-ray detectors are arranged with acquisition surfaces that are flat and parallel to one another. The acquisition surfaces face away from one another and respectively toward one of the breasts. At least one x-ray image of each breast is acquired while both breasts are simultaneously pressed against the support unit.

14 Claims, 2 Drawing Sheets

MAMMOGRAPHY METHOD AND MAMMOGRAPHY APPARATUS

BACKGROUND OF THE INVENTION

1. Field of the Invention

The present invention concerns a mammography method and a mammography apparatus suitable to implement the method.

2. Description of the Prior Art

Mammography is an x-ray examination of the breast with the goal of detecting tumors at an earliest possible stage. Through continuous improvement of mammography techniques it is sought to generate x-ray images with high significance in order to differentiate benign tissue variations from malignant variations and to reduce the number of incorrect findings, i.e. the number of suspicious findings that are caused by non-malignant variations and the number of undetected malignant tumors. In conventional x-ray mammography, a single two-dimensional image of the compressed breast is generated at a single projection direction. Since the tissue slices situated one after another in the direction of the x-ray beam are superimposed in such a projection, strongly absorbent benign structures can overlay a malignant tumor and hinder the ability to detect such a tumor.

In order to avoid this problem, a mammography technique known as tomosynthesis—in which individual images (exposures) of the breast are acquired with a digital x-ray detector in a number of different projection directions—is known from, for example, T. Wu et al., "Tomographic mammography using a limited number of low-dose cone-beam projection images", Med. Phys. 30, 365 (2003). A number of slice images that each represent a slice of the breast orientated parallel to the acquisition surface of the x-ray detector can then be reconstructed from these digital exposures acquired from different projection angles, i.e. from the image data belonging to these exposures. Such an image data set obtained by reconstruction is designated in the following as a tomosynthetic 3D x-ray image. Tissue structures that are situated deeper (as viewed in the propagation direction of the x-ray beam) can be detected better by using this measure.

Moreover, to improve tumor detection a digital mammography method is known in which a contrast agent that propagates in the blood vessels of the breast is intravenously injected into the patient after the generation of a first two-dimensional image. Such a method is described in Roberta A. Jong et al., "Contrast-enhanced Digital Mammography Initial Clinical Experience", Radiology 2003, Vol. 228, P. 842-850. The temporal propagation of the contrast agent that increasingly accumulates (enriches) at malignant lesions can be visualized in a number of exposures acquired in the same projection direction after the injection. The kinetics—i.e. the time curve of the enrichment—additionally indicates the presence of a malignant tumor.

A further development of this contrast agent-enhanced digital mammography method in which a first exposure is acquired with a low-energy x-ray beam and a second exposure is acquired with a high-energy x-ray beam, is known from J. M. Lewin et al., "Dual-energy contrast-enhanced digital subtraction mammography: feasibility", Radiology 2003, Vol. 229, P. 261-268. The energy spectrum of the low-energy x-ray beam is selected so that the contrast agent is practically invisible in that exposure, while the higher-energy x-ray beam is strongly absorbed by the contrast agent. A reference image, from which the structures of the normal breast tissue are largely eliminated and in which the contrast agent (which possibly accumulates only weakly due to the strong compression of the breast) is more clearly visible is generated from these exposures.

The contrast agents that are used are normally toxic and can be linked to unwanted side effects, such that their use should be limited to a minimum.

SUMMARY OF THE INVENTION

An object of the invention is to provide a mammography method in which the risks explained above accompanying the x-ray examinations implemented with the administration of a contrast agent are reduced. A further object of the invention is based to provide a mammography apparatus suitable to implement such a mammography method.

The first object is achieved according to the invention by a mammography method to generate x-ray images of a breast, wherein a support unit is positioned between the breasts, in which support unit are arranged two x-ray detectors with acquisition surfaces that are flat and parallel to one another, the acquisition surfaces face away from one another and respectively toward one breast; and at least one x-ray image of each breast is acquired while both breasts are simultaneously pressed against the support unit.

In this way both breasts are simultaneously located in a compressed state that is required for mammography, and given the use of two x-ray sources the right breast and left breast can either be acquired simultaneously or—given the use of only a single x-ray source—they can be acquired in series at a short time interval. By means of this immediate temporal proximity of the generation of the x-ray images of both breasts, in mammography methods in which a contrast agent is used this contrast agent must only be administered only once to the examination subject before the acquisition of the x-ray images.

This is particularly advantageous when the time curve of the propagation of the contrast agent should be recorded by the acquisition of multiple x-ray images in temporal succession.

With regard to a mammography apparatus, the above object according to the invention is achieved with a mammography apparatus having two compression plates that can be displaced perpendicular to their flat sides in the direction of a compression axis, with their flat sides aligned parallel to one another; and a support unit arranged between the compression plates, with two support surfaces situated opposite one another and respectively associated with a compression plate. Two x-ray detectors with flat acquisition surfaces respectively facing towards one of the support surfaces are arranged between the support surfaces. The mammography apparatus moreover includes an x-ray source that can be positioned in positions that are situated opposite one another relative to the bearing unit. In this way x-ray images of both breasts can be generated in temporal succession at short time intervals.

In a further embodiment of the apparatus, two x-ray sources are provided instead of one x-ray source. X-ray images of both breasts can be generated simultaneously in this way

DESCRIPTION OF THE PREFERRED EMBODIMENTS

Figure 1:
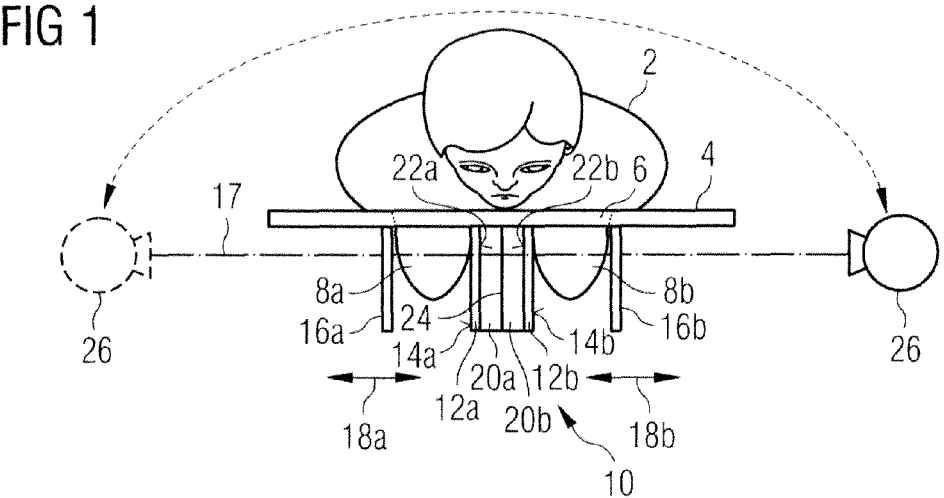
FIG. 1 shows a mammography apparatus according to the invention in plan view in the direction of the longitudinal axis of an examination subject (cranio-caudal direction).

According to FIG. 1, an examination subject 2 is located in ventral position on a patient table 4. In the patient table 4 is an opening through which both breasts 8a, 8b of the examination subject 2 protrude so that they project beyond the underside of the patient table 4. A support unit 10 that possesses two support plates 12a, 12b situated opposite one another is arranged below the patient bearing table 4, approximately central relative to the opening 6. The support plates 12a, 12b form support surfaces 14a and 14b situated opposite one another and respectively facing toward respective compression plates 16a, 16b. Compression plates 16a and 16b are aligned with their flat sides parallel to one another and are supported such that they can be displaced perpendicularly to their flat sides in the direction of a compression axis 17 (horizontal in the example). When the patient 2 lies face down on the table 4, the breast 8a is between the compression plate 16a and the support surface 14a, and the breast 8b is between the compression plate 16b and the support surface 14b. This displacement capability of the compression plates 16a, 16b is illustrated by double arrows 18a and 18b. Both breasts 8a, 8b are pressed and compressed against the support unit 10 by displacement of the compression plates 16a, 16b (that can also ensue in close temporal succession), such that they are simultaneously located in a compressed state required for the examination.

In the support unit 10, two x-ray detectors 20a, 20b are arranged between the support plates 12a, 12b and the support surfaces 14a, 14b. The flat acquisition surfaces 22a, 22b of the two x-ray detectors 20a, 20b are arranged parallel to one another and face away from one another so that they respectively face toward the support surfaces 14a and 14b, respectively, and one of the breasts 8a or 8b. Digital flat panel detectors are advantageously provided as x-ray detectors. Moreover, an x-ray-impermeable absorber layer 24 is advantageously arranged between the x-ray detectors 20a, 20b.

In the exemplary embodiment the mammography apparatus has an x-ray source 26 (for example an x-ray tube) with which a 2D x-ray image of the left breast 8b is initially generated in lateral projection (emanating from the lateral side) in a first position of the x-ray source 26. After an acquisition has occurred in the starting position shown in FIG. 1, the x-ray source 26 is brought into a second position that is opposite the starting position relative to the support unit 10, such that x-rays emitted in the second position propagate in the opposite direction as this is illustrated by the x-ray source 26 (depicted with a dashed line). In other words: in the first position the x-ray source 26 is facing toward the compression plate 16b and in the second position the x-ray source 26 is facing toward the compression plate 16a. In this second position a latero-medial 2D x-ray image of the right breast 8a is generated.

Figure 2:
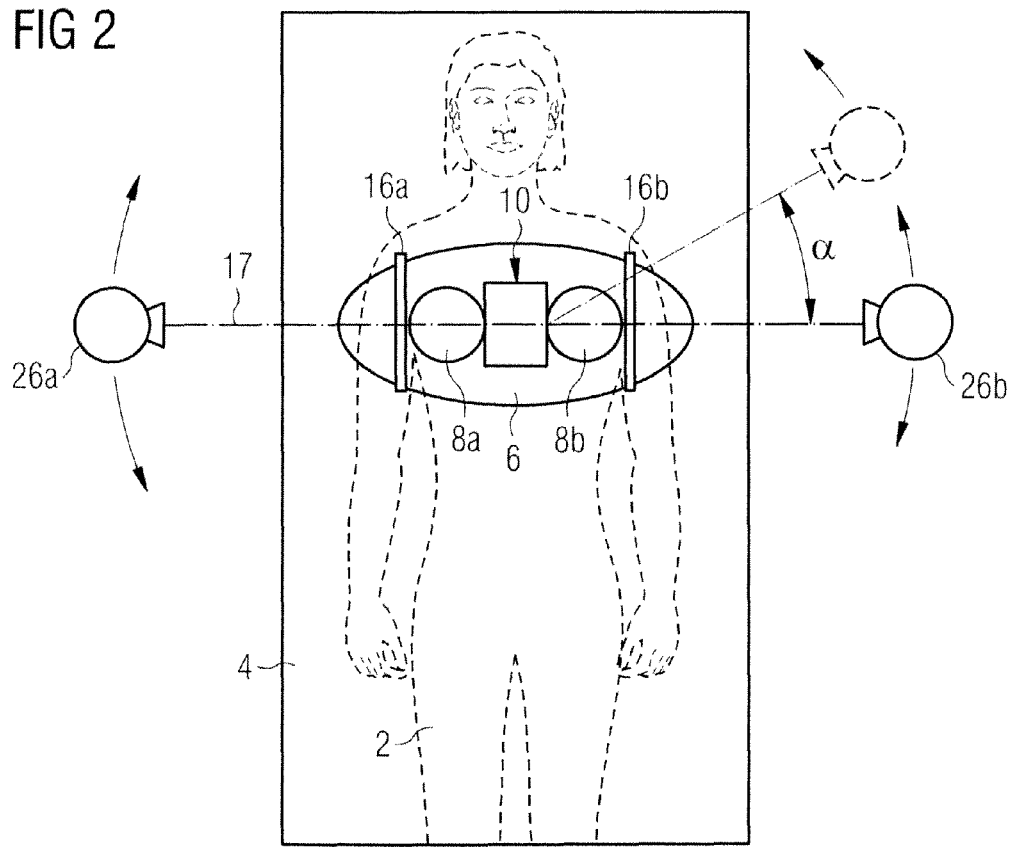
FIG. 2 shows an additional embodiment of a mammography apparatus according to the invention in a plan view in the direction of the sagittal axis of the examination subject, likewise in a schematic principle depiction.

In the exemplary embodiment according to FIG. 2, two x-ray sources 26a, 26b are provided that are arranged horizontally opposite one another in the home position. In the shown exemplary embodiment, these x-ray sources 26a, 26b can moreover be positioned in different positions so that x-ray exposures with different projection angles α relative to the normal of the acquisition surfaces 22a, 22b can be generated, with which exposures it is possible to reconstruct a tomosynthetic 3D x-ray image. For this purpose. the x-ray sources 26a, 22b are arranged so that they can be pivoted around an axis perpendicular to the plane of the drawing, as shown in FIG. 2.

As an alternative, it is also possible to generate exposures with different projection angles α with x-ray sources 26a, 26b that are mounted such that they can be displaced linearly, parallel to the flat sides of the detectors arranged in the support unit 10.

The generation of to osynthetic 3D x-ray images is in principle possible even if only a single x-ray source is used, as shown in FIG. 1.

Figure 3:
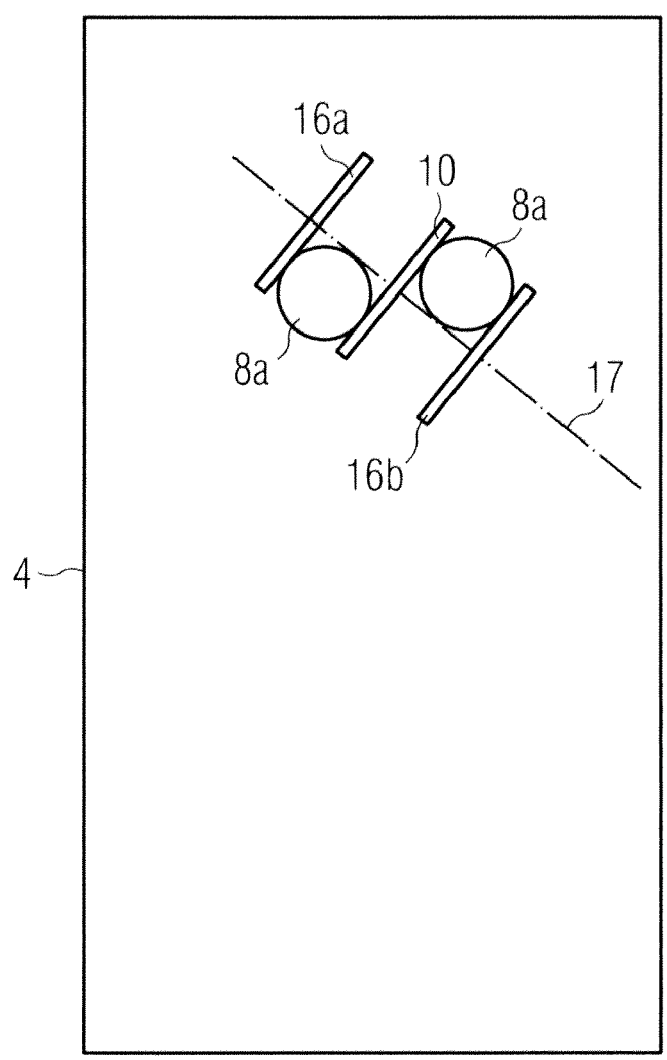
FIG. 3 shows an additional embodiment of a mammography apparatus according to the invention, likewise in a plan view in the direction of the sagittal axis of the examination subject.

In the exemplary embodiments shown in FIG. 1 and FIG. 2, the compression axis 17 runs in the lateral direction. In principle, however, the compression axis 17 can also run at an angle to this (as this is illustrated in FIG. 3) so that mammography exposures are possible in directions that are angled relative to the lateral direction (latero-medial oblique).

The mammography apparatus explained using FIG. 1 and FIG. 2 is particularly suitable for methods in which a contrast agent is administered to the examination subject 2 before the acquisition of the x-ray images. In this case it is sufficient to administer the contrast agent to the examination subject 2 once before the examination. A number of x-ray images of each breast 8a, 8b are subsequently acquired in temporal succession, and the time curve of the propagation of the contrast agent is registered in this way.

Independently of whether the time curve of the propagation should be recorded, it is advantageous for at least two x-ray images with x-rays of different energies to be generated from each breast in order to be able to generate in this way a reference image from which the structures of the normal breast tissue are largely eliminated. For this purpose, an x-ray source 26, or two x-ray sources 26a, 26b are provided that emit x-rays in energy ranges differing from one another. If energy-discriminating x-ray detectors are used, the two x-ray images can also be generated with a spectrally broadband x-ray source in a single exposure.

Although modifications and changes may be suggested by those skilled in the art, it is the intention of the inventor to embody within the patent warranted hereon all changes and modifications as reasonably and properly come within the scope of her contribution to the art.

I claim as my invention:

1. A mammography method to generate x-ray images of both breasts of a patient, comprising the steps of:
   providing a support unit with two x-ray detectors on opposite sides of the support unit, each of said x-ray detectors having a radiation detection surface that is flat, with the respective radiation detection surfaces being parallel to each other and facing away from each other;
   relatively positioning a patient and said support unit to cause said support unit to be located between the breasts of the patient with the detection surfaces being respectively adjacent the respective breasts of the patient;
   compressing each breast of the patient against the respective detection surface adjacent thereto; and
   exposing the breasts of the patient to x-ray radiation while both breasts are simultaneously pressed against the respective detection surfaces, and acquiring image data from each breast with the respective x-ray detectors, and emitting said image data at respective outputs of the respective x-ray detectors.

2. A mammography method as claimed in claim 1 wherein the step of exposing the breast to x-ray radiation comprises irradiating a first of the breasts with x-ray emitted from a first x-ray source and irradiating a second of the breast with x-rays emitted by a second x-ray source.

3. A mammography method as claimed in claim 1 wherein the step of exposing the breasts to x-ray radiation comprises irradiating each breast with x-ray radiation from a plurality of different projection angles and obtaining a projection image of each breast from each projection angle, and generating a tomosynthesis 3D x-ray image of each breast from the projection images thereof.

4. A mammography method as claimed in claim 1 comprising administering a contrast agent to the patient that enhances selected tissue in each breast prior to exposing the breasts to x-ray radiation.

5. A mammography method as claimed in claim 4 comprising acquiring a plurality of x-ray images of each breast in temporal succession that record a time curve of progression of said contrast agent in each breast.

6. A mammography method as claimed in claim 4 comprising acquiring at least two x-ray images of each breast by exposing each breast to x-rays having different energies and obtaining one x-ray image of each breast at each energy.

7. A mammography apparatus to generate x-ray images of both breasts of a patient, comprising:
 one x-ray source;
 a support unit with two x-ray detectors on opposite sides of the support unit, each of said x-ray detectors having a radiation detection surface that is flat, with the respective radiation detection surfaces being parallel to each other and facing away from each other;
 said support unit being configured for relative positioning thereof with respect to cause said support unit to be located between the breasts of the patient with the detection surfaces being respectively adjacent the respective breasts of the patient;
 compression plates that respectively compress each breast of the patient against the respective detection surface adjacent thereto; and
 said x-ray source being operable to expose the breasts of the patient to x-ray radiation while both breasts are simultaneously pressed against the respective detection surfaces, and said respective x-ray detectors acquiring image data from each breast and emitting said image data at respective outputs of the respective x-ray detectors.

8. A mammography apparatus as claimed in claim 7 comprising a rotatable mount at which said x-ray source is mounted for rotation around the breasts to irradiate each breast with x-ray radiation from a plurality of different projection angles and to obtain a projection image of each breast from each projection angle, and a computer configured to generate a tomosynthesis 3D x-ray image of each breast from the projection images thereof.

9. A mammography apparatus as claimed in claim 7 wherein said x-ray source is operable to acquire at least two x-ray images of each breast by exposing each breast to x-rays having different energies and to obtain one x-ray image of each breast at each energy.

10. A mammography method as claimed in claim 9 wherein said x-ray detectors are each energy-discriminating x-ray detectors.

11. A mammography apparatus to generate x-ray images of both breasts of a patient, comprising:
 two x-ray sources;
 a support unit with two x-ray detectors on opposite sides of the support unit, each of said x-ray detectors having a radiation detection surface that is flat, with the respective radiation detection surfaces being parallel to each other and facing away from each other;
 said support unit being configured for relative positioning thereof with respect to a patient to cause said support unit to be located between the breasts of the patient with the detection surfaces being respectively adjacent the respective breasts of the patient;
 compression plates that respectively compress each breast of the patient against the respective detection surface adjacent thereto; and
 said two x-ray sources being operable to respectively expose the breasts of the patient to x-ray radiation while both breasts are simultaneously pressed against the respective detection surfaces, and the respective x-ray detectors acquiring image data from each breast with the respective x-ray radiation from the two x-ray detectors, and emitting said image data at respective outputs of the respective x-ray detectors, said image data for one of the breasts being obtained from one of the two x-ray sources, and the image data for the other breast being obtained with the other of the two x-ray sources.

12. A mammography apparatus as claimed in claim 11 comprising a rotatable mount at which said two x-ray sources are mounted for rotation around the breasts to irradiate the respective breasts with x-ray radiation from a plurality of different projection angles to obtain a projection image of each breast from each projection angle, and a computer configured to generate a tomosynthesis 3D x-ray image of each breast from the projection images thereof.

13. A mammography apparatus as claimed in claim 11 wherein each of said two x-ray sources is operable to acquire at least two x-ray images of the respective breasts by exposing each breast to x-rays having different energies and obtaining one x-ray image of each breast at each energy.

14. A mammography method as claimed in claim 13 wherein said x-ray detectors are each energy-discriminating x-ray detectors.

* * * * *